(12) United States Patent
Chen et al.

(10) Patent No.: US 11,369,348 B2
(45) Date of Patent: Jun. 28, 2022

(54) ULTRASOUND DIAGNOSTIC APPARATUS, IMAGE PROCESSING APPARATUS, AND IMAGE PROCESSING METHOD

(71) Applicant: CANON MEDICAL SYSTEMS CORPORATION, Otawara (JP)

(72) Inventors: Qi Chen, Beijing (CN); Zhe Tang, Beijing (CN); Weijian Jian, Beijing (CN)

(73) Assignee: CANON MEDICAL SYSTEMS CORPORATION, Otawara (JP)

( * ) Notice: Subject to any disclaimer, the term of this patent is extended or adjusted under 35 U.S.C. 154(b) by 204 days.

(21) Appl. No.: 16/526,598

(22) Filed: Jul. 30, 2019

(65) Prior Publication Data

US 2020/0037995 A1 Feb. 6, 2020

(30) Foreign Application Priority Data

Jul. 31, 2018 (CN) .......................... 201810856451.3

(51) Int. Cl.
*A61B 8/00* (2006.01)
*A61B 8/08* (2006.01)
(Continued)

(52) U.S. Cl.
CPC .......... *A61B 8/5207* (2013.01); *A61B 8/0891* (2013.01); *A61B 8/14* (2013.01);
(Continued)

(58) Field of Classification Search
CPC ....... A61B 8/5207; A61B 8/0891; A61B 8/14; A61B 8/5238; A61B 5/055; A61B 5/0035;
(Continued)

(56) References Cited

U.S. PATENT DOCUMENTS 8,111,892 B2  2/2012 Hyun et al.
2014/0193053 A1  7/2014 Kadoury et al.
(Continued)

FOREIGN PATENT DOCUMENTS

CN  101216939 A  7/2008
CN  103402453 A  11/2013
(Continued)

OTHER PUBLICATIONS

Chinese Office Action dated Nov. 3, 2021, issued in Chinese Patent Application No. 201810856451.3.

*Primary Examiner* — Joel Lamprecht
(74) *Attorney, Agent, or Firm* — Oblon, McClelland, Maier & Neustadt, L.L.P.

(57) ABSTRACT

An ultrasound diagnostic apparatus includes processing circuitry. The processing circuitry generates a first image based on an echo signal obtained by transmission and reception of ultrasound waves. The processing circuitry acquires a second image that is an image generated by a medical image diagnostic apparatus. The processing circuitry performs a registration of the first image and the second image, by discretely setting a plurality of relative positions of the first image and the second image within a specified range, calculating the similarity between the first image and the second image corresponding to the plurality of relative positions respectively, updating the plurality of the relative positions based on the calculation result of the similarity, and recalculating the similarity corresponding to the plurality of the updated relative positions respectively. The processing circuitry causes a display to display the images obtained after the registration.

16 Claims, 7 Drawing Sheets

(51) Int. Cl.
*G06T 7/30* (2017.01)
*A61B 8/14* (2006.01)
*A61B 5/055* (2006.01)

(52) U.S. Cl.
CPC ............... *G06T 7/30* (2017.01); *A61B 5/055* (2013.01); *A61B 8/5238* (2013.01); *G06T 2207/10088* (2013.01); *G06T 2207/30056* (2013.01); *G06T 2207/30101* (2013.01)

(58) Field of Classification Search
CPC ........... A61B 5/7425; A61B 8/00; G06T 7/30; G06T 2207/10088; G06T 2207/30101; G06T 2207/30056; G06T 2207/10132
See application file for complete search history.

(56) References Cited

U.S. PATENT DOCUMENTS

| | | | |
|---|---|---|---|
| 2015/0294467 A1* | 10/2015 | Blumhofer | G06T 7/30 |
| | | | 382/131 |
| 2016/0007970 A1* | 1/2016 | Dufour | A61B 8/58 |
| | | | 600/437 |
| 2016/0174902 A1* | 6/2016 | Georgescu | G06T 7/0012 |
| | | | 600/408 |
| 2018/0028157 A1 | 2/2018 | Li et al. | |
| 2018/0064422 A1* | 3/2018 | Otomaru | G06T 7/33 |

FOREIGN PATENT DOCUMENTS

| | | |
|---|---|---|
| JP | 2009-112468 A | 5/2009 |
| JP | 2016-508406 A | 3/2016 |
| WO | WO 2016/136065 A1 | 9/2016 |

\* cited by examiner

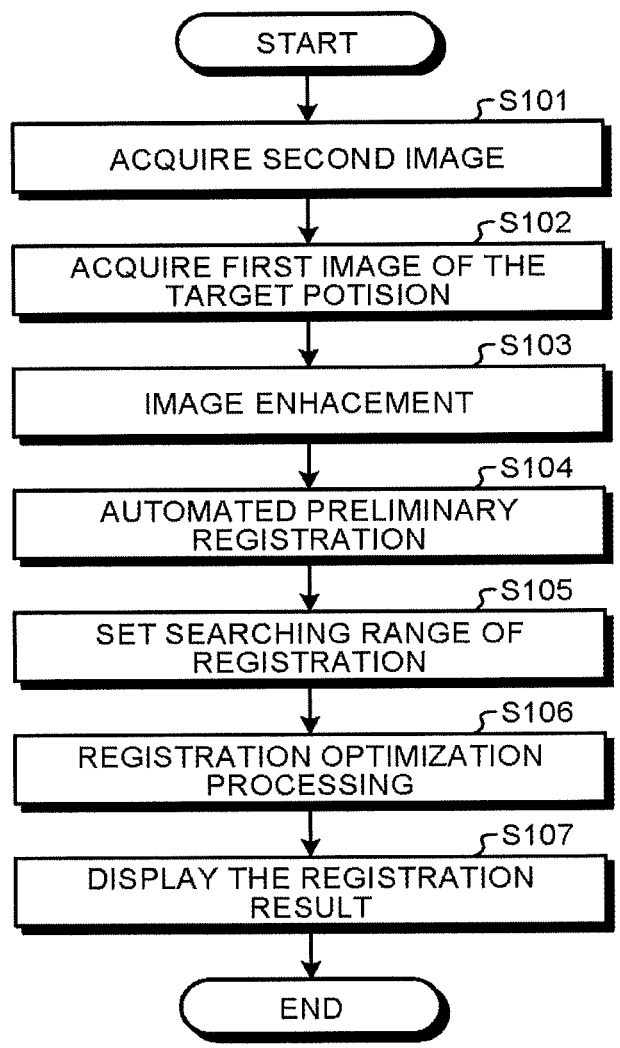

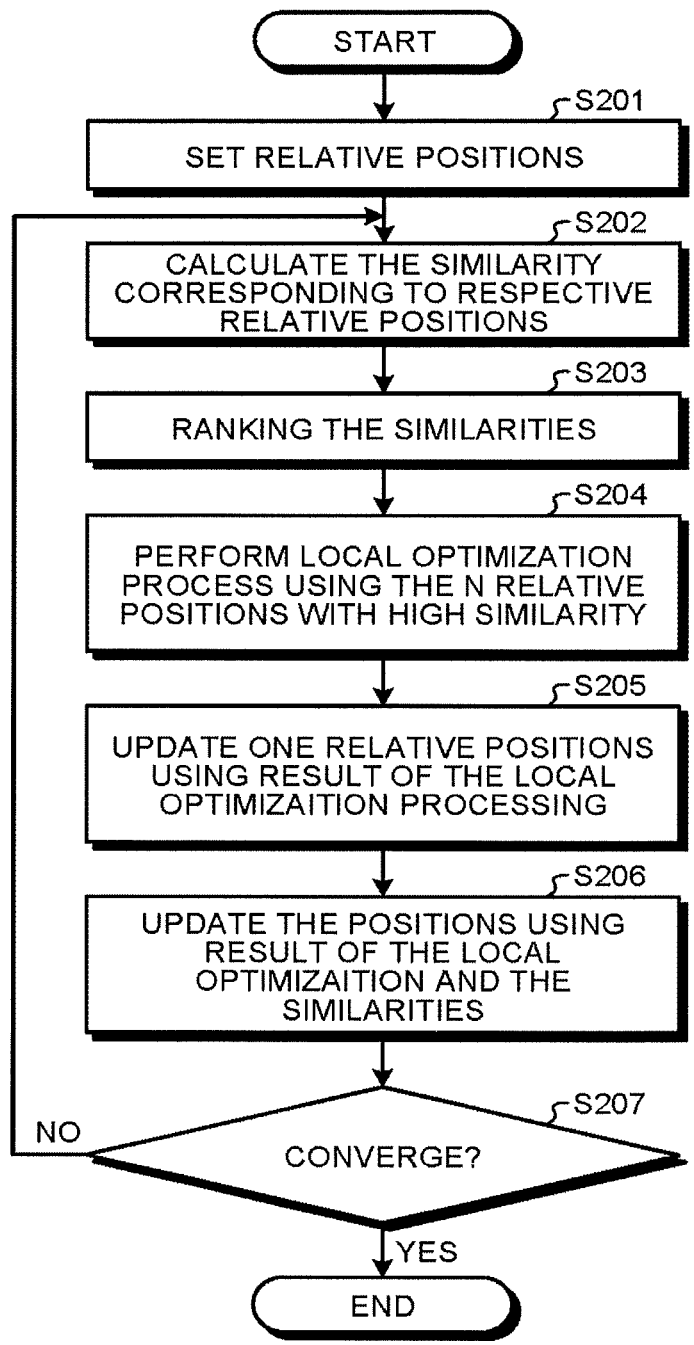

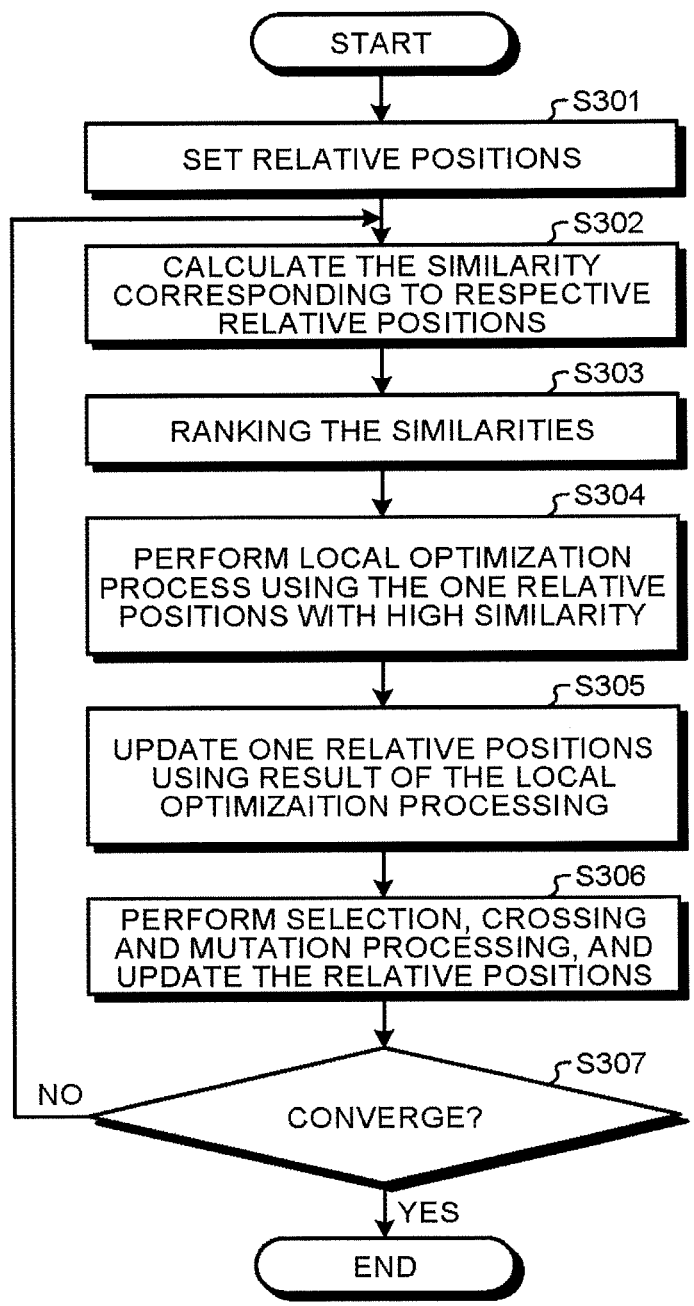

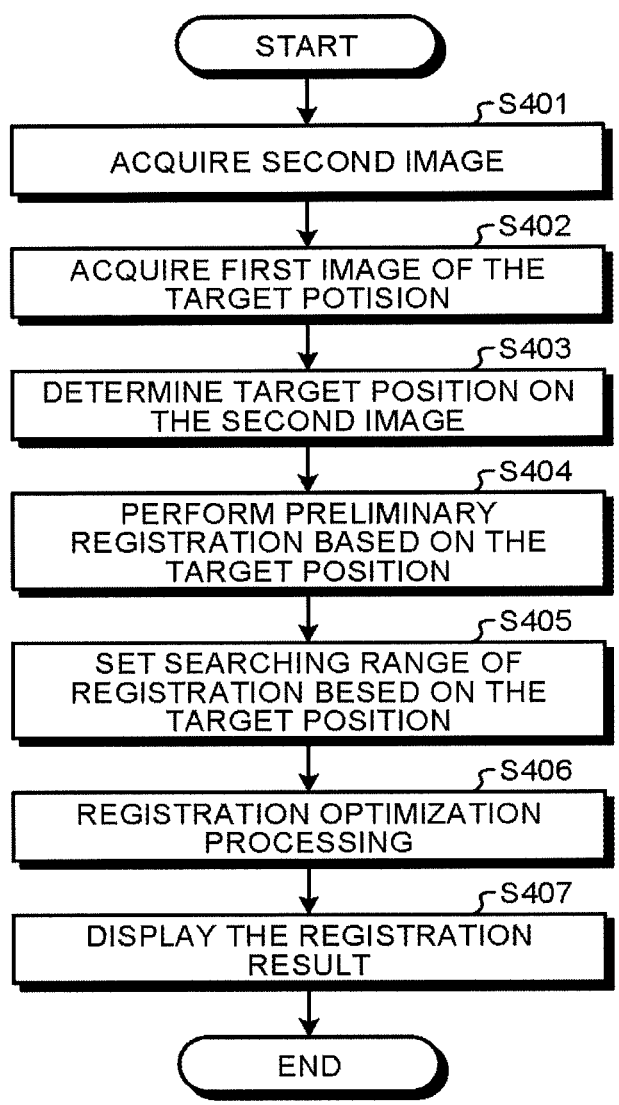

ULTRASOUND DIAGNOSTIC APPARATUS, IMAGE PROCESSING APPARATUS, AND IMAGE PROCESSING METHOD

CROSS-REFERENCE TO RELATED APPLICATIONS

This application is based upon and claims the benefit of priority from Chinese Patent Application No. 201810856451.3, filed on Jul. 31, 2018, the entire contents of which are incorporated herein by reference.

FIELD

Embodiments described herein relate generally to an ultrasound diagnostic apparatus, an image processing apparatus, and an image processing method.

BACKGROUND

In current ultrasound diagnostic apparatus or medical image processing apparatus, by registration of medical images such as US images (ultrasound images), CT (Computed Tomography) images, MRI (Magnetic resonance imaging) images or the like, doctors can be effectively assisted to identify target lesions, such as tumours or the like. Moreover, since ultrasound imaging is advantageous in that it is real-time and convenient, image processing methods in which ultrasound is fused with MRI or CT images are popular.

In brief, registration between ultrasound images and CT/MRI images refers to aligning the positions of the ultrasound images with the positions of the CT/MRI images by searching for precise image rotation and translation. The registration between the ultrasound image and the CT/MRI image is actually a process of finding an optimal mapping from the ultrasound image space to the CT/MRI image space.

Usually, due to the limited scanning range of the ultrasound scanning probe, the data of one ultrasound image may be scanned from different scanning angles and only contain a small field of vision (FOV), such as a partial volume of a particular organ. Therefore, it is necessary to search for the amount of rotation and the amount of translation of the image in a relatively large searching range to perform registration of the ultrasound image and the CT/MRI image.

As a technique for narrowing the image searching range at the time of registration, feature extraction is usually performed on two or more target images, and preliminary registration is performed by using the extracted features, and then registration of the target image in a further localized range is performed by a local optimization algorithm.

Feature extraction of medical images in the prior art typically involves segmentation of blood vessels and segmentation of surfaces (e.g., surfaces of organs). In order to be able to extract features from ultrasound images, it is desirable to be able to acquire the following two types of ultrasound images: one is an ultrasound image that can see as many views of the vessel tree as possible so as to conduct vessel segmentation and vascular structure identification, and the other is an ultrasound image with a scan area as large as possible so as to be used in surface segmentation.

However, in practice, it is difficult for an operator performing an ultrasound scan to scan both the target region (e.g., a tumor region) and the blood vessel or surface. In order to ensure the accuracy of feature extraction, it is required to acquire a large number of ultrasound images, and there is also a high requirement for the ability of the operator to acquire the ultrasound image.

In addition, in case that the accuracy of feature extraction based on the ultrasound image is not high, the preliminary registration result may be inaccurate, and it may even be possible to erroneously align different features together. In case that the searching range of the subsequent registration optimization process is not large, the final registration result will probably be erroneous.

BRIEF DESCRIPTION OF THE DRAWINGS

FIG. 2 is a flowchart showing the image registration performed by the ultrasound diagnostic apparatus according to the first embodiment;

FIG. 3 is a flow chart showing the registration optimization process of FIG. 2;

FIG. 4 is a flow chart showing a variant of the registration optimization process of FIG. 2;

FIG. 7 is a flowchart showing image registration performed by the ultrasound diagnostic apparatus according to a second embodiment.

DETAILED DESCRIPTION

Figure 1:
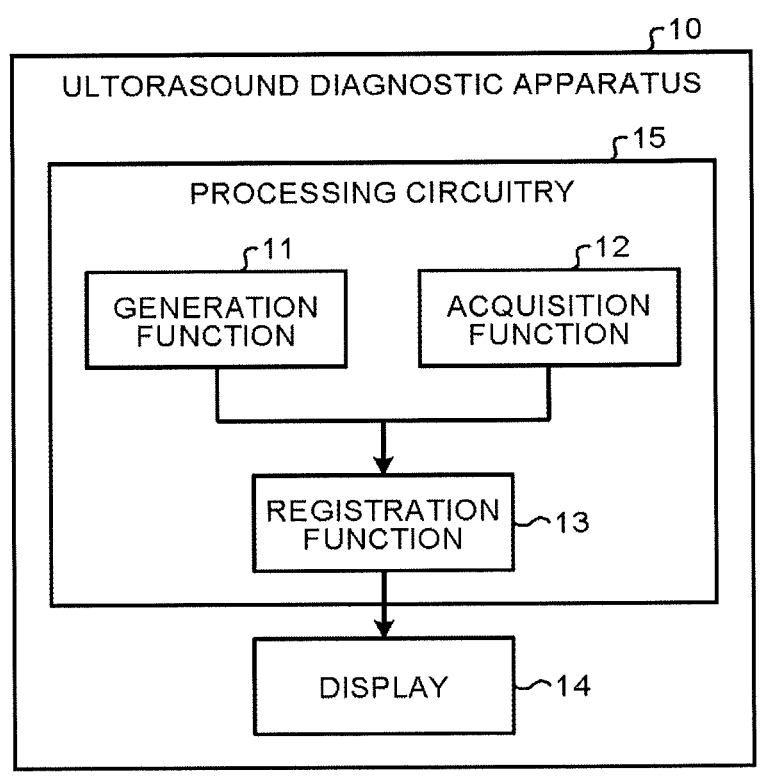
FIG. 1 is a block diagram showing the structure of an ultrasound diagnostic apparatus according to a first embodiment.

According to an embodiment, an ultrasound diagnostic apparatus includes processing circuitry. The processing circuitry is configured to generate a first image based on an echo signal obtained by transmission and reception of ultrasound waves. The processing circuitry is configured to acquire a second image that is an image generated by a medical image diagnostic apparatus. The processing circuitry is configured to perform a registration of the first image and the second image. The processing circuitry is configured to cause a display to display the images obtained after the registration. The processing circuitry is configured to discretely set a plurality of relative positions of the first image and the second image within a specified range. The processing circuitry is configured to calculate the similarity between the first image and the second image corresponding to the plurality of relative positions respectively. The processing circuitry is configured to update the plurality of the relative positions based on the calculation result of the similarity. The processing circuitry is configured to recalculate the similarity corresponding to the plurality of the updated relative positions respectively.

In order to address the above issues, an ultrasound diagnostic apparatus, an image processing apparatus, and an image processing method capable of facilitating the operation of image registration and of improving the accuracy of the image registration are proposed.

An ultrasound diagnostic apparatus according to the present embodiment comprising: a generation function for generating a first image based on an echo signal obtained by transmission and reception of ultrasound waves; an acquisition function for acquiring a second image that is an image generated by the medical image diagnostic apparatus; a registration function for registering the first image and the second image; and a display for displaying the image obtained after the registration, the ultrasound diagnostic apparatus is characterized in that, the registration function discretely sets a plurality of relative positions of the first image and the second image within a specified range, calculates the similarity between the first image and the second image corresponding to the plurality of relative positions respectively, updates the plurality of the relative positions based on a calculation result of the similarity, and recalculates the similarity corresponding to the updated relative positions respectively.

An image processing method according to the present embodiment comprising: a generation step for generating a first image based on an echo signal obtained by transmission and reception of ultrasound waves; an acquisition step for acquiring a second image that is an image generated by the medical image diagnostic apparatus; a registration step for registering the first image and the second image; and a display step for displaying the image obtained after the registration, the image processing method is characterized in that, in the registration step: using the plurality of positions discretely set for the second image to change the relative position between the first image and the second image, calculate the similarities between the first image and the second image corresponding to the respective relative positions and meanwhile update the plurality of the relative positions based on the calculation result of the similarity, and recalculate the similarity using the updated plurality positions.

The image processing apparatus of the present embodiment comprising: a first acquisition function for acquiring an ultrasound image as a first image; a second acquisition function for acquiring a second image generated by the medical image diagnostic apparatus or the image processing apparatus; and a registration function for registering the first image and the second image, the ultrasound diagnostic apparatus is characterized in that, in the registration function: using a plurality of positions discretely set for the second image to change the relative position between the first image and the second image, calculate the similarity between the first image and the second image corresponding to the respective relative positions and meanwhile update the plurality of the relative positions based on the calculation result of the similarity, and recalculate the similarity using the updated plurality positions.

The image processing method of the present embodiment comprising: a first acquisition step for acquiring an ultrasound image as a first image; a second acquisition step for acquiring a second image generated by the medical image diagnostic apparatus or the image processing apparatus; and a registration step for registering the first image and the second image, the image processing method is characterized in that, in the registration step: using a plurality of positions discretely set for the second image to change the relative position between the first image and the second image, calculate the similarity between the first image and the second image corresponding to the respective relative positions and meanwhile update the plurality of the relative positions based on the calculation result of the similarity, and recalculate the similarity using the updated plurality positions.

In the ultrasound diagnostic apparatus or method of the present embodiment, a plurality of relative positions of the first image and the second image are set within a specified range, the similarity between the first image and the second image is calculated for the plurality of relative positions, and the relative positions are updated based on the calculation results of the similarity.

Thereby, the dependence on the extraction of features of blood vessels, surfaces and the like in the image is reduced as compared with the previous image registration method in which the preliminary registration is performed by feature extraction, thereby reducing requirements of the number of acquisitions of ultrasound images, the way of acquisition and the like, making the image registration processing easier. Moreover, the case that the final registration fails due to the low accuracy of feature extraction is avoided, and the accuracy of image registration is improved.

In the following, embodiments of the ultrasound diagnostic apparatus of the present application will be described in detail with reference to the drawings. The embodiments shown in the present embodiment are merely illustrative and are not limited to the constructions shown in the embodiments.

First Embodiment

FIG. 1 is a block diagram showing the structure of an ultrasound diagnostic apparatus relating to a first embodiment of the present embodiment.

As shown in FIG. 1, the ultrasound diagnostic apparatus 10 according to the first embodiment includes processing circuitry 15 and a display 14. The processing circuitry 15 includes a generation function 11, an acquisition function 12, and a registration function 13. In the present example, the processing circuitry 15 is an example of the processing circuitry.

In the ultrasound diagnostic apparatus 10 shown in FIG. 1, the processing functions are stored in memory (not shown) in the form of computer-executable programs. The processing circuitry 15 is a processor configured to realize the functions corresponding to the programs by reading and executing the programs from the memory. In other words, the processing circuitry 15 that has read the programs has the functions corresponding to the read programs. FIG. 1 illustrates the example in which the processing functions, namely, the generation function 11, the acquisition function 12, and the registration function 13 are realized by the single processing circuitry (i.e., the processing circuitry 15); however, possible embodiments are not limited to this example. For instance, the processing circuitry 15 may be structured by combining together a plurality of independent processors, so that the processing functions are realized as a result of the processors executing the programs. Further, the processing functions of the processing circuitry 15 may be realized as being distributed or integrated in one or more processing circuits, as appropriate.

The processing circuitry 15 executes processes performed by the generation function 11 described below, by reading and executing a program corresponding to the generation function 11 from the memory. The generation function 11 obtains an echo signal by transmitting and receiving ultrasound waves, and generates an ultrasound image as a first image based on the echo signal. More specifically, the ultrasound diagnostic apparatus 10 further includes a probe (not shown) for transmitting and receiving ultrasound waves, and the probe transmits the received echo wave to the generation function 11, thereby the generation function 11 generates the ultrasound image. The ultrasound image in the present embodiment is a three-dimensional stereoscopic image.

The processing circuitry 15 executes processes performed by the acquisition function 12 described below, by reading and executing a program corresponding to the acquisition function 12 from the memory. The acquisition function 12 acquires a second image. The second image is an image generated by a medical image diagnostic apparatus such as an ultrasound diagnostic apparatus, a CT diagnostic apparatus, or a MRI diagnostic apparatus or the like. The second image in the present embodiment will be illustrated by taking a CT image generated by a CT apparatus or a MRI image generated by a MRI apparatus as an example. The way the acquisition function 12 acquires the second image can be, for example, acquired from the medical image diagnostic apparatus via a network (Internet or local area network). The second image in the present embodiment is a three-dimensional stereoscopic image.

The processing circuitry 15 executes processes performed by the registration function 13 described below, by reading and executing a program corresponding to the registration function 13 from the memory. The registration function 13 registers the first image generated by the generation function 11 and the second image acquired by the acquisition function 12. The specific actions regarding the registration will be described in detail later.

A display 14 displays the image obtained after registration. The display may can be in such a way that a fused image of the first image and the second image is displayed, or the first image and the second image after registration can be displayed side by side.

Next, with reference to FIG. 2, an image registration operation performed by the ultrasound diagnostic apparatus 10 of the first embodiment will be described.

First, in step S101, the acquisition function 12 of the ultrasound diagnostic apparatus 10 acquires a CT image or a MRI image as a second image.

Next, in step S102, the operator scans the target position of the organ expected to be inspected. During the scanning process, the user does not need to consider the scanning of the organ features in the ultrasound image, and only needs to scan the ultrasound wave to the target position. For example, in the case that the target position of the organ to be examined is the entire liver or a certain region of the liver, the operator only needs to ensure that the target position is scanned, and it is not necessary to ensure that the features of the blood vessel and the surface of the liver are clearly scanned. As mentioned above, when the registration is performed by using the shape of a blood vessel, the surface of an organ, or the like, it is not possible to accurately perform the registration when the shape cannot be extracted or is extracted inaccurately. To cope with this situation, the registration according to the present embodiment does not rely on the shape of a blood vessel, the surface of an organ, or the like, but the registration is performed by using gradients of brightness levels or the like between the first image and the second image, as described below. In addition, the order of the execution of steps S101 and S102 is interchangeable.

Next, in step 3103, the registration function 13 performs enhancement processing on the first image and the second image. Specifically, the structures depicted in the first image and the second image are enhanced. The enhancement processing includes noise filtering processing, enhancement processing of intensity and contrast, and blood vessel enhancement processing.

Next, in step S104, the registration function 13 performs a preliminary registration on the first image and the second image.

As described above, the first image and the second image are both three-dimensional stereoscopic images, therefore, registering the two images requires the rotation and/or translation of at least one of them. The transform parameters of the image include rotation parameters and translation parameters. The rotation parameters include the rotation angle of the X axis, the rotation angle of the Y axis, and the rotation angle of the Z axis. The translation parameters include the moving distance along the X axis, the moving distance along the Y axis, and the moving distance along the Z axis.

Since the optimization power of the registration optimization algorithm in the following step S106 is strong, the preliminary registration in this step has low requirements on the registration accuracy, and only a simple registration between the first image and the second image is required.

The simple registration may align only the center points of the first image and the second image (in other words, make the center of the ultrasound image located at the center of the CT/MRI image), and the initial values of the rotation angles of the X-axis, the Y-axis, and the Z-axis are all set to 0°, and the initial values of the moving distances of the X-axis, the Y-axis, and the Z-axis are all set to 0 mm.

In addition, the initial values of the transform parameters (rotation angle and movement distance) can also be set to an average value. For example, the initial values of each transform parameters are set based on the average value of previous registration results.

Next, in step S105, the registration function 13 sets the searching range of the registration. In the present embodiment, since the accuracy of the preliminary registration in step S103 is low and since the orientation of the organ contained in the first image may significantly be different from the orientation of the organ contained in the second image in some situations, it is necessary to set the searching range of the registration to the global searching range.

For example, when a tumor in the liver is to be examined, an ultrasound image may be acquired, in some situations, by an ultrasound probe that is pressed sideways against a side of the body of the examined subject (the patient). In that situation, because the orientation of the liver contained in the ultrasound image is significantly different from the orientation of the liver contained in the CT image or the MRI image, there is a long movement distance between the state in which the simple preliminary registration process has been performed and the state in which the registration has been performed to have the positions accurately aligned. Accordingly, in the present embodiment, the searching range of the registration set in step S105 is large. The global searching range means that the rotation angle is defined as a global angular range, and the movement distance is also defined as a global translation range.

The global searching range is defined as follows:
X-axis rotation: $-180°\sim+180°$
Y-axis rotation: $-180°\sim+180°$
Z axis rotation: $-180°\sim+180°$
X-axis translation: $-W/2\sim+W/2$
Y-axis translation: $-H/2\sim+H/2$
Z axis translation: $-D/2\sim+D/2$ Wherein W is the larger one of the length of the first image in the X direction and the length of the second image in the X direction, and H is larger one of the length of the first image in the Y direction and the length of the second image in the Y direction, and D is the larger one of the length of the first image in the Z direction and the length of the second image in the Z direction. For example, The units of W, H, and D are pixels or millimeters.

For example, assuming that W, H, and D all equals to 200 mm, the above global searching range is defined as:
X-axis rotation: −180°~+180°
Y-axis rotation: −180°~+180°
Z axis rotation: −180°~+180°
X-axis translation: −100 mm~+100 mm
Y-axis translation: −100 mm~+100 mm
Z axis translation: −100 mm~+100 mm Next, in step S106, the registration function 13 performs registration optimization processing of the first image and the second image. Specifically, the registration function discretely sets a plurality of relative positions of the first image and the second image within a specified range, calculates the similarity between the first image and the second image corresponding to each of the plurality of relative positions respectively, updates the plurality of the relative positions based on a calculation result of the similarity, and recalculates the similarity corresponding to the updated relative positions respectively. When the similarity reaches the specified level or the relative position is no longer updated, the optimization process ends.

As used herein, the "similarity of the first image and the second image" can be calculated in various ways, for example, it can be calculated based on the similarity magnitude such as the gradient value of the image, the gray value, or the image correlation. As used herein, the "specified range" refers to the global searching range set in step S105.

More specifically, the registration function 13 calculates the similarity of each of the plurality of relative positions that is observed when the relative positional relationship between the first image and the second image is changed within the global searching range set in step S105. In the present embodiment, the plurality of relative positions are set, not by continuously changing the relative positional relationship between the first image and the second image, but by discretely changing the relative positional relationship. In other words, in the present embodiment, there may be, in some situations, a long movement distance between the state in which the simple preliminary registration process has been performed and the state in which the registration has been performed to have the positioned accurately aligned. Thus, if the plurality of relative positions were set by continuously changing the relative positional relationship between the first image and the second image, the number of processes required before the registration optimization process converges would increase, and there would also be a possibility that the registration optimization process might converge by mistake, without conducting a search in the entire global searching range.

To cope with this situation, for example, the registration function 13 sets the plurality of relative positions so that the plurality of relative positions indicating the positional relationship between the first image and the second image are distributed throughout the entire global searching range. In one example, the registration function 13 sets the relative positions in a plurality of locations so as to be evenly distributed in the global searching range. Further, the registration function 13 calculates the similarity of each of the relative positions set in the plurality of locations and further updates each of the relative positions based on the calculated similarities. The registration function 13 performs the registration on the first image and the second image, by repeatedly performing the calculation of the similarities and the updating of the relative positions, until a predetermined condition is satisfied.

Next, in step S107, the display 14 displays the registration result. When the registration optimization process converges, the first image and/or the second image has found the optimal rotation angle and movement distance. These values are used as transformation matrices (transformation parameters), and CT/MRI images or ultrasound images are transformed, and the images obtained after registration are displayed.

Next, the detailed operation of the registration optimization processing in step S106 will be described with reference to FIG. 3.

In the registration optimization processing of the present embodiment, the algorithm of the objective function is a metric value using a combination of gradient and gray scale as a similarity calculation function for performing optimization. The ultimate goal of the optimization method is to find the maximum value of the objective function. In other words, the registration optimization process is to search for relative positions that maximize the similarities, by repeatedly performing the calculation of the similarities and the updating of the relative positions.

In step S201, a plurality of relative positions of the first image and the second image are discretely set within a specified range.

Next, in step S202, the similarity between the first image and the second image corresponding to the plurality of relative positions respectively are calculated.

Next, in step S203, the plurality of calculated similarities are ranked.

Then, in step S204, a local optimization processing is performed using N relative positions with high similarity among the plurality of similarities calculated in step S202. Here, for example, N=7.

The local optimization process in this embodiment employs the Downhill simplex algorithm. The Downhill simplex algorithm is an algorithm that optimizes the input parameter data in a small local range. The detailed description regarding the optimization process of the Downhill simplex algorithm will be omitted.

In step S204, the N relative positions with high similarity among the plurality of similarities are used as the input parameter data of the Downhill simplex algorithm to initialize the simplex, and the optimized result of the Downhill simplex algorithm calculated thereby act as the current optimal similarity (group optimal value) in the multiple relative positions and the optimal relative position corresponding to the optimal similarity.

For example, in the local optimization process, while taking into consideration a historical optimal value of each of the N relative positions having the high similarities, the optimization is performed on one of the N relative positions. In one example, in the local optimization process, the optimization is performed while taking into consideration the historical optimal value of the relative position having the highest similarly among the N relative positions and the historical optimal values of the other relative positions. In this situation, the historical optimal value denotes the value exhibiting the highest similarity while the registration optimization process is repeatedly performed.

Next, in step S205, any one of the plurality of relative positions is updated using the result of the local optimization process. In other words, any one of the plurality of relative positions is replaced with the optimal relative position corresponding to the optimal similarity obtained in step S204. For example, the relative position having the highest similarity among the N relative positions is replaced with the optimal relative position corresponding to the optimal similarity.

Next, in step S206, the registration function 13 updates each of the plurality of relative positions using the plurality of similarities calculated in step S202 and the optimal similarity calculated in step S205.

For example, for each of a plurality of relative positions, a historical optimum value of the relative position itself and a current optimal value of the plurality of relative positions (i.e., the current optimal similarity) are considered, the relative position is optimized (updated). Of course, the way to optimize (update) multiple relative positions is not limited to this.

Next, it is determined in step S207 whether the optimization result converges, in other words, it is determined whether the similarity has reached a specified level. Each optimization method contains an objective function, and the goal of optimization is to make the function value to reach the maximum, when the optimization cannot find a larger object value, it can be determined that the optimization result converges. Here, "the similarity reaches the specified level" means that the similarity reaches a predetermined degree of convergence. For example, if the difference between the similarity calculated after the Mth update of the relative position and the similarity calculated after the M−1th update of the relative position is smaller than a predetermined value (for example, 10−4), it is regarded that the similarity has reached the predetermined degree of convergence. Further, after it is determined that the similarity has reached the specified level, the relative positions of the first image and the second image are no longer updated.

If the determination in step S207 is "NO", the process returns to step S202, and steps S202 to S206 are performed repeatedly. On the other hand, if the determination in step S207 is YES, the registration optimization processing ends.

The technical effects of the present embodiment will be described below.

Step S201, step S202, step S203, step S206, and step S207 in the present embodiment employ a global optimization algorithm of Particle Swarm Optimization (PSO). Step S204 employs a local optimization algorithm of the Downhill simplex algorithm.

In the Particle Swarm Optimization algorithm, each relative position in the above embodiments is also referred to as a particle, and each particle is an individual optimization point having attributes such as rotation and translation or the like, and its adaptation value is determined by the optimization function, and the speed determines the direction and distance of the movement. The particle swarm algorithm first initializes a group of random particles and then finds the optimal solution through iteration. In each iteration, each particle updates itself by tracking the individual historical optimal value and the entire population to the current moment to find the global optimal value to find the optimal particle in the search space, and using the rotation and/or translation of the optimal particle as the final transform parameter.

In this embodiment, one or more relative positions with high similarity calculated in the global optimization algorithm are substituted into the local optimization algorithm (step S203), and the obtained current optimal similarity is fed back to the global optimization algorithm (Step S205).

The local optimization algorithm can speed up the optimization process to obtain the optimal value.

By combining the global optimization algorithm and the local optimization algorithm, the global optimization capability and the local optimization capability of the algorithm are simultaneously improved, therefore, it is only necessary to simply register the first image and the second image before performing the registration optimization process.

Moreover, the combination of the global optimization algorithm and the local optimization algorithm can cope with a larger searching range, and can avoid the occurrence of inaccurate registration results due to the small searching range of the registration optimization process.

Moreover, the image registration method of the present embodiment reduces the dependence on the extraction of features of blood vessels, surfaces and so forth in the image, therefore, during the ultrasound scanning process, the user does not need to consider the scanning of the organ features in the ultrasound image, and only needs to simply scan the ultrasound wave to the target location. Thereby, the requirements for the number of acquisition of the ultrasound image, the acquisition method or the like are reduced, and the convenience of the ultrasonic scanning operation is improved.

Moreover, the enhancement processing of the image in step 103 can improve the accuracy of the similarity calculation, thereby the accuracy of the registration optimization processing in step S106 can be improved. For example, when the similarity calculation of the first image and the second image is performed in step S106, the gradient value is used, and the gradient is enhanced by the enhancement processing of the image, thereby it is advantageous for improving the accuracy of the optimization result.

Of course, other similarity measures other than the gradient value and the gray scale value can be used.

Variation of the First Embodiment

In the first embodiment, the global optimization algorithm employs a Particle Swarm Optimization algorithm, and the local optimization algorithm employs a Downhill simplex algorithm, but actually it is not limited to this.

The global optimization algorithm can also employ other algorithms such as Genetic algorithm or the like, the local optimization algorithm can also employ any one of the Powell algorithm, the Gradient descent algorithm, the Conjugate gradient algorithm, the Quasi-Newton algorithm, and the Levenberg-Marguardt algorithm.

In the following variation of the first embodiment, an example in which the global optimization algorithm employs a genetic algorithm and the local optimization algorithm employs a gradient descent algorithm is shown. This variation is only different from the first embodiment in the registration optimization process (step S106), and in the following, description will be made emphasizing the distinctive points.

FIG. 4 is a flow chart showing a variant of the registration optimization process of FIG. 2.

In the steps shown in FIG. 4, steps S301 to S303 and step S305 are substantially the same as steps S201 to S203 and S205 in the first embodiment, and repeated description will be omitted.

In step S304, one relative position with the highest similarity among the plurality of similarities is used as the input parameter data of the Gradient descent algorithm, and the optimization result of the Gradient descent algorithm calculated thereby becomes the current optimal similarity among the plurality of relative positions, along with the optimal relative position corresponding to the optimal similarity. The detailed description of the calculation process of the Gradient descent algorithm will be omitted here.

In addition, after step S305, for the current plurality of relative positions, based on the composition of the Genetic algorithm, processes of selection, crossing, and mutation are performed, and then an update on the plurality of relative positions obtained after the processing is performed.

Similarly, the above-described modification can also have the technical effects of the first embodiment.

Figure 5C:
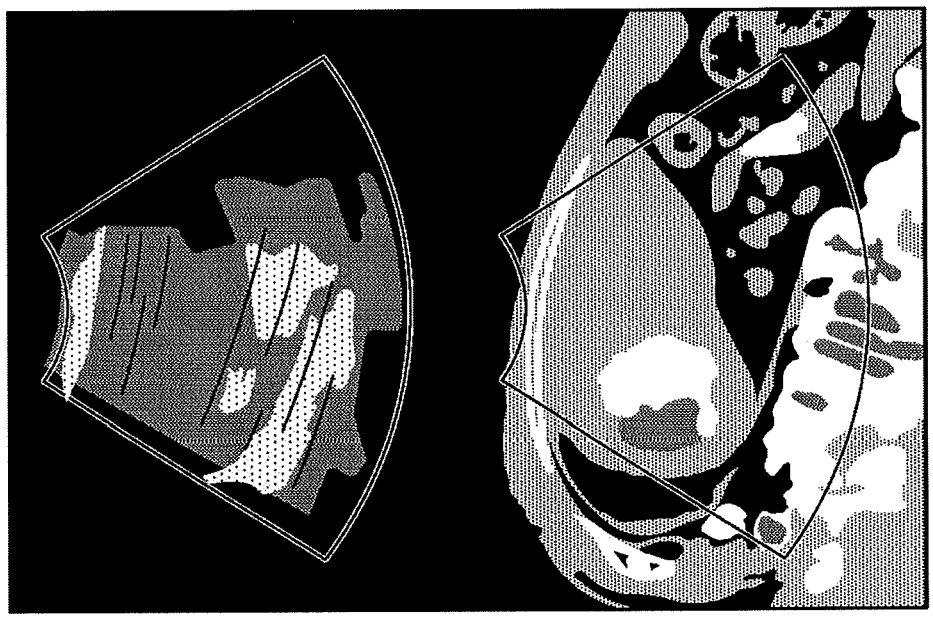
FIG. 5C is a schematic diagram showing an example of the ultrasound image and the CT image after the registration.
Figure 5A:
FIG. 5A is a schematic diagram showing an example of the CT image before registration.
Figure 5B:
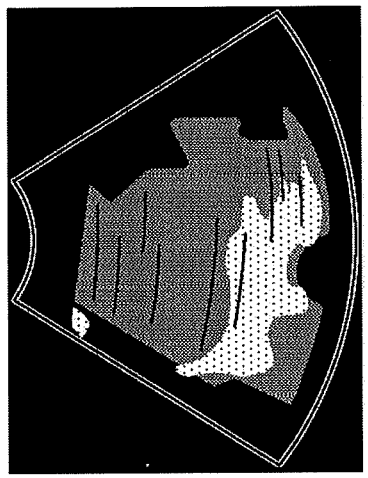
FIG. 5B is a schematic diagram showing an example of the ultrasound image before registration.
Figure 6C:
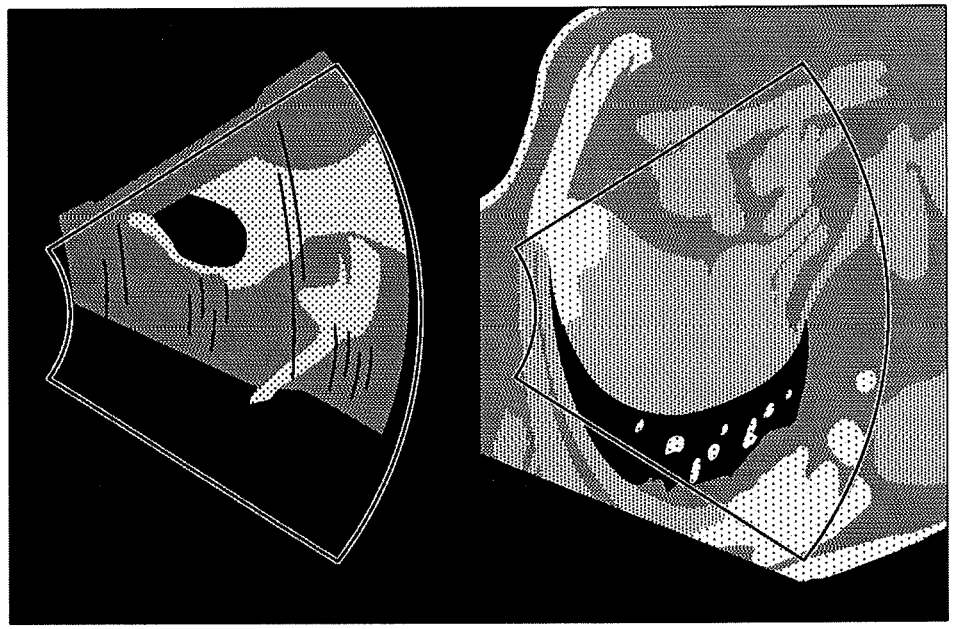
FIG. 6C is a schematic diagram showing an example of the ultrasound image and the MRI image after the registration.
Figure 6A:
FIG. 6A is a schematic diagram showing an example of the MRI image before the registration.
Figure 6B:
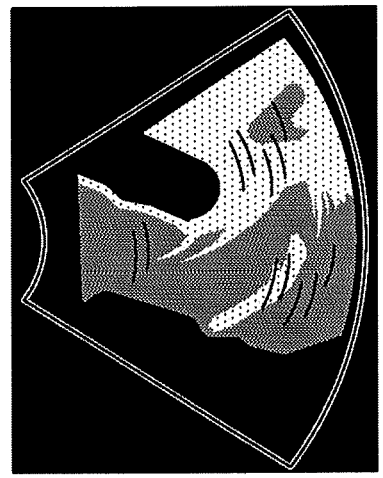
FIG. 6B is a schematic diagram showing an example of the ultrasound image before the registration.

FIG. 5A is a schematic diagram showing an example of the CT image before registration. FIG. 5B is a schematic diagram showing an example of the ultrasound image before registration. FIG. 5C is a schematic diagram showing an example of the ultrasound image and the CT image after the registration. FIG. 6A is a schematic diagram showing an example of the MRI image before the registration. FIG. 6B is a schematic diagram showing an example of the ultrasound image before the registration. FIG. 6C is a schematic diagram showing an example of the ultrasound image and the MRI image after the registration.

FIG. 5A is a CT image acquired in step S101, FIG. 5B is an ultrasound image acquired in step S102, and FIG. 5C is an image showing the registration result in step 107.

After the registration optimization process converges, the CT/MRI image or the ultrasound image is transformed using the searched optimal rotation angle and moving distance as a transform matrix (transform parameter). At this time, it is possible to transform only one of the images, or to transform both images at the same time.

In FIG. 5C, in order to more clearly observe the target region, i.e., the area marked with x in FIG. 5A, an example in which both images are transformed is shown. Further, in FIG. 5C, the way that the two images are displayed in a fused manner is not employed, but the way that the first image and the second image after registration are displayed side by side is employed. Moreover, a fan shape corresponding to the boundary of the upper ultrasound image is also displayed in the CT image of FIG. 5C, thereby both can be observed for comparison more conveniently.

FIG. 6A is a MRI image acquired in step S101, FIG. 6B is an ultrasound image acquired in step S102, and FIG. 6C is an image showing a registration result in step 107.

Similar to FIG. 5, in FIG. 6C, in order to more clearly observe the target region, an example in which both images are transformed is shown. Further, in FIG. 6C, the way that the first image and the second image after registration are displayed side by side is also employed. Moreover, a fan shape corresponding to the boundary of the upper ultrasound image is also displayed in the MRI image of in FIG. 6C.

Second Embodiment

In the following, a second embodiment of the present embodiment will be described.

In the second embodiment, the registration function 13 reduces the specified range (global searching range) based on the sites contained in the first image or the diagnostic purpose of the first image, and performs registration using the reduced range. Moreover, the step of image enhancement is omitted in the second embodiment.

FIG. 7 is a flowchart showing image registration performed by the ultrasound diagnostic apparatus 10 according to a second embodiment. In the respective steps shown in FIG. 7, steps other than steps S403 to S405 are the same as those in the first embodiment, and repeated descriptions will be omitted here.

In step S403, the target position is determined on the CT/MRI image. The process of determining the target position can be determined by the operator. For example, in the case that the CT/MRI image shows that a part of the lower right region of the liver has a tumor, the operator determines the part of the lower right region of the liver as the target region.

In addition, the action of determining the target region can also be automatically performed by techniques such as image recognition.

In step S404, a preliminary registration is performed based on the determined target position. Unlike the simple registration in the first embodiment, the first image and the second image may be aligned by taking the target position or a position close to the target position as the center, and the initial values of the rotation angles of the X-axis, the Y-axis, and the Z-axis are set to an angle at which the target position can be easily scanned by ultrasound. This is because that at an angle easy to perform ultrasonic scanning on the target position, there is a high possibility of obtaining a clear image of the target position.

In step S405, the searching range of registration is set based on the target position. Corresponding to the target location, the global searching range is reduced. For example, some rotation angles and areas at which it is difficult to clearly observe the target range are removed.

In the case that a part of the lower right region of the liver is determined as the target region, the global searching range, for example can be defined as:

X-axis rotation: $-180°\sim+180°$
Y-axis rotation: $-180°\sim+180°$
Z axis rotation: $-60°\sim+180°$
X axis translation: $-W/2\sim0$
Y-axis translation: $-H/2\sim+H/2$
Z axis translation: $-D/2\sim0$ Wherein W is the larger one of the length of the first image in the X direction and the length of the second image in the X direction, and H is larger one of the length of the first image in the Y direction and the length of the second image in the Y direction, and D is the larger one of the length of the first image in the Z direction and the length of the second image in the Z direction. The units of W, H, and D are, for example, pixels or millimeters.

In the second embodiment, a preliminary registration of the first image and the second image is performed based on the target position, and the accuracy of the preliminary registration can be improved. Moreover, narrowing the searching range of the registration optimization process based on the target position can effectively reduce the amount of calculation and reduce the time required for the registration optimization process.

(Other Variants)

Several embodiments of the present application have been described above, however, these embodiments are presented as examples, and is not intended to limit the scope of the present embodiment. These embodiments can be implemented in various other ways, various omission, exchange and alternation can be made without departing from the scope of the spirit of the present embodiment. These embodiments or the variation thereof are included in the scope and spirit of the present embodiment and also include in the present embodiment recited within the scope of the claims and equivalents thereof.

The concept of the present embodiment can also be applied to other image processing apparatuses. For example, The image processing apparatus of the present embodiment comprising: a first acquisition function for acquiring an ultrasound image as a first image; a second acquisition function for acquiring a second image generated by a medical image diagnostic apparatus or an image processing apparatus; and a registration function for registering the first image and the second image, the ultrasound diagnostic apparatus is characterized in that, in the registration function: using a plurality of positions discretely set for the second image, changing the relative position between the first image and the second image and meanwhile calculating the similarity between the first image and the second image corresponding to the respective relative positions, updating the plurality of the relative positions based on the calculation result of the similarity, and recalculating the similarity using the updated plurality positions.

In the embodiments described above, the example is explained in which the registration is performed on the ultrasound image and the other medical image; however possible embodiments are not limited to this example. The present disclosure may be applied to registration of medical images other than ultrasound images. For example, the present disclosure may be applied to registration between a CT image and an MRI image. In that situation, for example, an image processing apparatus includes: an acquisition function for acquiring a first image and a second image generated by either a medical image diagnostic apparatus or the image processing apparatus; and a registration function for registering the first image and the second image. The registration function discretely sets a plurality of relative positions of the first image and the second image within a specified range and calculates similarities between the first image and the second image corresponding to the plurality of relative positions, respectively. Further, the registration function updates the plurality of relative positions based on a calculation result of the similarities, and recalculates similarities corresponding to the updated plurality of relative positions, respectively. As a result, for example, it is possible to perform accurate image registration, when a CT image and an MRI image are displayed side by side, or when an ultrasound image, a CT image, and an MRI image are displayed side by side.

The ultrasound diagnostic apparatus and image processing apparatus of the present embodiment can be equipped in the medical device as a circuit that can fulfill the functions described above, can also be distributed as a program executable by a computer or other electronic device, stored in a storage media such as magnetic disk (floppy disk (floppy, registered trademark), hard disk etc.), optical disk (CD-ROM, DVD etc.), optical magnetic disk (MO), semiconductor memory and the like, and can be performed by the processor of a computer or an electronic device.

In each of the above embodiments, the case in which the first image and the second image are three-dimensional stereoscopic images has been described. Actually, the first image can be any one of a two-dimensional image, a three-dimensional image, and a dynamic image, and the second image can be any one of a three-dimensional image and a dynamic image. Further, the type of the second image may also be an ultrasound image generated by the ultrasound device.

The image registration described in the above embodiments may be used, for example, when an ultrasound image is acquired and displayed in a real-time manner so as to perform a manipulation, while viewing a CT image as a reference image. In other words, as a result of performing the registration between the CT image and the ultrasound image, it is possible to constantly display a CT image that is substantially in the same position as the ultrasound image acquired through a scan performed by an ultrasound probe and displayed in the real-time manner. The practitioner is therefore able to perform the manipulation while constantly viewing the CT image that is substantially in the same position as the real-time ultrasound image.

During the manipulation described above, the positional relationship between the ultrasound image and the CT image resulting from the registration may come out of alignment due to a body movement of the examined subject (the patient) or the like. In that situation, the practitioner needs to perform the image registration again. At that time, by using the technique of the present disclosure, the practitioner is able to perform the registration between the ultrasound image that is two-dimensional and the CT image that is three-dimensional. Accordingly, even when the two-dimensional ultrasound image is being acquired during the manipulation, it is possible to perform the image registration again, without the trouble of acquiring a three-dimensional ultrasound image.

In addition, in step S103, the registration function 13 performs enhancement processing on both the first image and the second image, in fact, depending on the actual requirement, only the first image or only the second image may be enhanced, or no enhancement is performed at all.

In various embodiments, the registration function 13 repeatedly performs the sheet registration optimization processing until the similarity reaches a specified level. In fact, even if the registration optimization process of the combination of the global optimization algorithm and the local optimization algorithm of the present embodiment is performed only once, a faster and more accurate registration result than the prior art can be obtained, and the occurrence of inaccurate registration results due to the small searching range of the registration optimization process can be avoided.

In the second embodiment, an example in which the searching range is narrowed based on the target position is described. In addition, other anatomical structures such as ribs and the like can also be used to narrow the search.

For example, if there is no restriction, the searching range of the rotation angles is usually −180° to +180°, but if we have rib information, the searching range of the rotation angles should follow the rib structure and the probe should be in between two ribs. In this case, by excluding the rotation angles at which the target region cannot be scanned, the searching range of the rotation angle can be set to a value smaller than 360°. In addition, the information of the ribs can be obtained by other images, so that the action of limiting the searching range based on the rib information can be done automatically.

The term "processor" used in the above description of the first and the second embodiments denotes, for example, a Central Processing Unit (CPU), a Graphics Processing Unit (GPU), or a circuit such as an Application Specific Integrated Circuit (ASIC) or a programmable logic device (e.g., a Simple Programmable Logic Device [SPLD], a Complex Programmable Logic Device [CPLD], or a Field Programmable Gate Array [FPGA]). The one or more processors realize the functions by reading and executing the programs saved in the memory.

The embodiments are explained above by using the example in which the single memory device stores therein the programs corresponding to the processing functions;

however, another arrangement is also acceptable in which a plurality of memory devices are arranged in a distributed manner, so that the processing circuit is configured to read a corresponding program from each of the individual memory devices. Further, instead of saving the programs in the one or more memory devices, it is also acceptable to directly incorporate the programs into the circuits of the one or more processors. In that situation, the one or more processors realize the functions by reading and executing the programs incorporated in the circuits thereof.

Further, the constituent elements of the apparatuses and the devices described in the above embodiments are based on functional concepts. Thus, it is not necessary to physically configure the constituent elements as indicated in the drawings. In other words, the specific modes of distribution and integration of the apparatuses and the devices are not limited to those illustrated in the drawings. It is acceptable to functionally or physically distribute or integrate all or a part of the apparatuses and the devices in any arbitrary units, depending on various loads and the status of use. Further, all or an arbitrary part of the processing functions performed by the apparatuses and the devices may be realized by a CPU and a program that is analyzed and executed by the CPU or may be realized as hardware using wired logic.

Further, the image processing methods explained in the above embodiments may be realized by causing a computer such as a personal computer or a workstation to execute an image processing program prepared in advance. The image processing program may be distributed via a network such as the Internet. Further, the control program may be recorded on a computer-readable non-transitory recording medium such as a hard disk, a flexible disk (FD), a Compact Disk Read-Only Memory (CD-ROM), an MO disk, a Digital Versatile Disk (DVD), or the like, so as to be executed as being read from the recording medium by a computer.

According to at least one aspect of the embodiments described above, it is possible to facilitate the operation of the image registration and to improve the accuracy of the image registration.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

What is claimed is:

1. An ultrasound diagnostic apparatus, comprising:
processing circuitry configured to
generate a first image based on an echo signal obtained by transmission and reception of ultrasound waves;
acquire a second image that is an image generated by a medical image diagnostic apparatus;
perform a registration of the first image and the second image; and
cause a display to display an image obtained by performing the registration, wherein the processing circuitry is configured to perform the registration by:
discretely setting a plurality of relative positions of the first image and the second image so that the plurality of relative positions are distributed throughout a specified range,
calculating similarities between the first image and the second image corresponding to the plurality of relative positions respectively,
selecting at least one relative position from the plurality of relative positions based on a plurality of similarities calculated for each relative position,
updating the plurality of relative positions by performing an optimization process using the at least one selected relative position, and
recalculating the similarity corresponding to the updated plurality of relative positions respectively.

2. The ultrasound diagnostic apparatus according to claim 1, wherein the processing circuitry is configured to
reduce the specified range according to sites contained in the first image or a diagnostic purpose of the first image, and
perform the registration using the reduced range.

3. The ultrasound diagnostic apparatus according to claim 1, wherein the relative position is a position indicated by at least one of a rotation angle and a movement distance of the first image with respect to the second image.

4. The ultrasound diagnostic apparatus according to claim 1, wherein the first image is any one of a two-dimensional image, a three-dimensional image and a dynamic image, and the second image is any one of a three-dimensional image and a dynamic image.

5. The ultrasound diagnostic apparatus according to claim 1, wherein the processing circuitry is configured to perform, as a pre-processing for calculating the similarity, an enhancement processing at least on structures delineated in the first image.

6. The ultrasound diagnostic apparatus according to claim 1, wherein the processing circuitry is configured to
calculate an optimal similarity and a relative position corresponding to the optimal similarity from a history information of the similarity for more than one relative position with high similarity among the calculation results of the similarity,
use the calculation result of the similarity and the calculation result of the optimal similarity to update the plurality of relative positions.

7. The ultrasound diagnostic apparatus according to claim 6, wherein the processing circuitry is configured to
use a global optimization algorithm to calculate a similarity between the first image and the second image corresponding to the plurality of relative positions respectively,
use a local optimization algorithm to calculate the optimal similarity and the relative position corresponding to the optimal similarity, based on the history information of the similarity at each relative position,
use the global optimization algorithm to update the plurality of relative positions of the second image.

8. The ultrasound diagnostic apparatus according to claim 7, wherein
the global optimization algorithm is any one of a particle swarm algorithm and a genetic algorithm,
the local optimization algorithm is any one of a downhill simplex algorithm, a Powell algorithm, a gradient descent algorithm, a conjugate gradient algorithm, a quasi-Newton algorithm, and a Levenberg-Marquartt algorithm.

9. The ultrasound diagnostic apparatus according to claim 1, wherein the processing circuitry is configured to
repeatedly perform: calculating the similarity between the first image and the second image corresponding to the plurality of relative positions respectively, updating the plurality of relative positions based on the calculation result of the similarity, and recalculating the similarity corresponding to the updated plurality of relative positions respectively, until the similarity reaches a specified degree.

10. An image processing method, comprising:
generating a first image based on an echo signal obtained by transmission and reception of ultrasound waves;
acquiring a second image generated by a medical image diagnostic apparatus;
performing a registration of the first image and the second image, by discretely setting a plurality of relative positions of the first image and the second image so that the plurality of relative positions are distributed throughout a specified range, calculating the similarity between the first image and the second image corresponding to the plurality of relative positions respectively, selecting at least one of relative position from the plurality of relative positions based on a plurality of similarities calculated for each relative position, updating the plurality of relative positions by performing an optimization process using at least one selected relative position, and recalculating the similarity corresponding to the updated plurality of relative positions respectively; and
causing a display to display an image obtained by performing the registration.

11. An image processing apparatus, comprising:
processing circuitry configured to
acquire a first image and a second image generated by a medical image diagnostic apparatus or the image processing apparatus; and
perform a registration of the first image and the second image, wherein the processing circuitry is configured to perform the registration by:
discretely setting a plurality of relative positions of the first image and the second image so that the plurality of relative positions are distributed throughout a specified range,
calculating the similarity between the first image and the second image corresponding to the plurality of relative positions respectively,
selecting at least one of relative position from the plurality of relative positions based on a plurality of similarities calculated for each relative position,
updating the plurality of relative positions by performing an optimization process using at least one selected relative position, and
recalculating the similarity corresponding to the updated plurality of relative positions respectively.

12. An image processing method, comprising:
acquiring a first image and a second image generated by a medical image diagnostic apparatus or an image processing apparatus; and
performing a registration of the first image and the second image, by discretely setting a plurality of relative positions of the first image and the second image so that the plurality of relative positions are distributed throughout a specified range, calculating similarities between the first image and the second image corresponding to the plurality of relative positions respectively, selecting at least one of relative position from the plurality of relative positions based on a plurality of similarities calculated for each relative position, updating the plurality of relative positions by performing an optimization process using at least one selected relative position, and recalculating the similarity corresponding to the updated plurality of relative positions respectively.

13. The ultrasound diagnostic apparatus according to claim 1, wherein the processing circuitry is configured to
calculate an optimal similarity based on an objective function and calculate a relative position corresponding to the optimal similarity from a history information of the similarity for more than one relative position with high similarity among the calculation results of the similarity,
use the calculation result of the similarity and the calculation result of the optimal similarity to update the plurality of relative positions.

14. The ultrasound diagnostic apparatus according to claim 6, wherein the processing circuitry is configured to
use a global optimization algorithm based on an objective function to calculate a similarity between the first image and the second image corresponding to the plurality of relative positions respectively,
use a local optimization algorithm based on the objective function to calculate the optimal similarity and the relative position corresponding to the optimal similarity, based on the history information of the similarity at each relative position,
use the global optimization algorithm to update the plurality of relative positions of the second image.

15. The ultrasound diagnostic apparatus according to claim 14, wherein
the global optimization algorithm is any one of a particle swarm algorithm and a genetic algorithm,
the local optimization algorithm is any one of a downhill simplex algorithm, a Powell algorithm, a gradient descent algorithm, a conjugate gradient algorithm, a quasi-Newton algorithm, and a Levenberg-Marquartt algorithm.

16. The ultrasound diagnostic apparatus according to claim 1, wherein the calculating the similarity between the first image and the second image corresponding to the plurality of relative positions respectively comprises calculating the similarity using a combination of a gradient and gray scale.

\* \* \* \* \*